Figure 1:
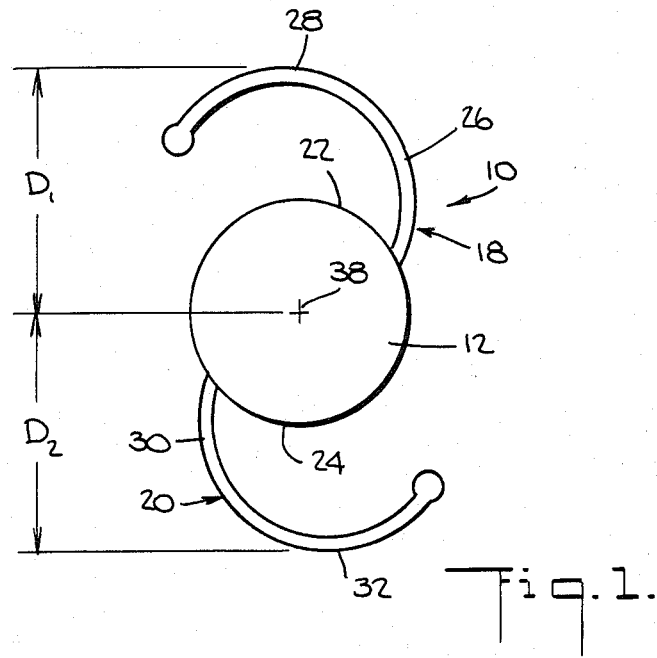

United States Patent [19]
Kelman

[11] Patent Number: 4,524,468
[45] Date of Patent: Jun. 25, 1985

[54] INTRAOCULAR LENSES

[76] Inventor: Charles D. Kelman, North Shore Towers, 269 Grand Central Pkwy. Bldg. 3, Floral Park, N.Y. 11005

[21] Appl. No.: 494,306

[22] Filed: May 13, 1983

[51] Int. Cl.³ ............................ A61F 1/16; A61F 1/24
[52] U.S. Cl. .......................................................... 623/6
[58] Field of Search .......................................... 3/13, 1

[56] References Cited

U.S. PATENT DOCUMENTS

| | | | |
|---|---|---|---|
| 4,253,200 | 3/1981 | Kelman | 3/13 |
| 4,403,353 | 9/1983 | Tennant | 3/13 |

FOREIGN PATENT DOCUMENTS 2084024  4/1982  United Kingdom ...................... 3/13

*Primary Examiner*—Ronald L. Frinks
*Attorney, Agent, or Firm*—Henry Sternberg

[57] ABSTRACT

An intraocular lens with a medial light-focusing lens body includes oppositely disposed position fixation members having seating portions that are respectively resiliently retained between vascular and non-vascular portions of the eye. The position fixation members are formed of different materials for beneficial cooperation with the respective portions of the eye.

10 Claims, 2 Drawing Figures

INTRAOCULAR LENSES

This invention relates to intraocular lenses for the human eye and more particularly to an intraocular lens having support members of different materials.

The insertion of an intraocular lens in the eye is a well known and widely used technique for restoring vision after a cataract removal operation. The natural structure of the eye furnishes a variety of locations for fixing the position of an intraocular lens in the eye. For example, an intraocular lens can be supported posteriorly of the iris as disclosed in my U.S. Pat. No. 4,253,200.

While it may be desirable to support the intraocular lens posteriorly of the iris between the anterior and posterior capsule walls without suturing, such positioning cannot always be achieved because the extent of anterior wall structure at the upper portion of the eye that remains after cataract surgery is usually insufficient to accommodate and hold a position fixation member of the intraocular lens without suturing. Therefore, other locations in the eye which do not require sutures must be considered.

It has been found that a posterior chamber, two-loop intraocular lens such as described in my U.S. Pat. No. 4,253,200 can be positioned without sutures with one of its loops positioned superiorly in the ciliary sulcus of the eye between the iris and the anterior capsule wall and with the other of its loops positioned inferiorly in the posterior capsule. These seating regions are at different distances from the optical axis of the eye, however, so that the lens must be made to compensate for such difference. According to my own U.S. Pat. No. 4,253,200, posterior chamber lenses are known which compensate for the different distances by having position fixation members of different lengths, or of different flex characteristics to facilitate sealing one such member in the capsule and the other position fixation member in the ciliary sulcus. My aforesaid patent also teaches that it is possible to achieve the different flex characteristics for compensating for the different seating distances by using materials of different stiffness. Such posterior chamber, two-loop intraocular lenses may comprise a medial light-focusing lens body with a pair of oppositely disposed, dimensionally equivalent, position fixation members in the general shape of a J. The J-shaped position fixation members are usually formed of a plastic such as polypropylene having sufficient spring-like quality to provide a resilient seating of the lens body in the ciliary sulcus of the eye on the one hand, and in the posterior capsule of the eye on the other hand. Although such resilient contact of the position fixation members provides stable positioning of the lens body in the eye without sutures, several problems may be encountered with such lenses made entirely of polypropylene. For example, it is my belief that polypropylene is not sufficiently inert and consequently cases irritation to the vascular tissue of the ciliary sulcus and resultant adhesion of such tissue to the position fixation member which is seated in the ciliary sulcus. Such adhesion could result in substantial difficulties if it were desired to remove the lens at a later date. On the other hand, known intraocular lenses having both their position fixation members of polymethylmethacrylate exhibit other problems, for example, polymethylmethacrylate is much stiffer than polypropylene and therefore a lens with two polymethylmethacrylate legs will tend to exert too much pressure on the ciliary sulcus resulting in irritation of that region, also the leg seated in the capsule will tend not to be as well anchored due to the biological properties of polymethylmethacrylate.

Among the several objects of the present invention may be noted the provision of an intraocular lens having two oppositely disposed position fixation members, one of which is adapted to be resiliently retained in the ciliary sulcus and the other of which is adapted to be resiliently retained between the anterior and posterior capsule walls, which is easier to insert and a short time after implantation exerts less overall force on the ciliary sulcus than known posterior chamber, two-loop polymethylmethacrylate intraocular lenses, and which, I believe, is substantially less irritating and easier to remove from the eye, should such become desirable at some later date, than known two-loop polypropylene lenses.

Other objects and features will be in part apparent and in part pointed out hereinafter.

The present invention relates to a novel intraocular lens having a lens body with two oppositely disposed position fixation members, one of the position fixation members being adapted to be seated in the ciliary sulcus and the other position fixation member being adapted to be seated in the capsule. To facilitate description of the structure disclosed herein it will be presumed that the eye has an optical axis passing through the center of the pupil. It will also be presumed that when the intraocular lens is inserted in an optimum position in the eye the optical axis of the lens body is in substantial alignment with the optical axis of the eye.

While there are known intraocular lenses having their position fixation members entirely of polymethylmethacrylate and there are known lenses having their position fixation members entirely of polypropylene, each of these lens types has specific advantages and disadvantages when used in the posterior chamber of an eye. The posterior chamber intraocular lens according to the present invention combines these materials in a novel manner so as to derive the most advantageous characteristics of each and to eliminate the most disadvantageous characteristics of each. The lens according to the present invention has its upper position fixation member formed of polymethylmethacrylate and its lower position fixation member formed of polypropylene.

Since the deflective stiffness of these materials is substantially different, when equal forces are exerted against the seating portions of each position fixation member the softer polypropylene member will deflect a substantially greater amount than the much stiffer polymethylmethacrylate member. In fact, under the force conditions normally prevailing in the average human eye, it is believed that most, if not all of the combined deflection of the pair of sealing portions of an implanted lens according to this invention, will be accounted for by the polypropylene member.

In an average human eye the distance from the optical axis of the eye to the inner peripheral surface of the ciliary sulcus is approximately one millimeter greater than the distance from the optical axis to the inner peripheral surface of the circumferential cul-de-sac portion of the eye formed between the anterior and posterior capsule walls. So as to accommodate this difference in distance and still obtain maximum benefit from both the springiness characteristics as well as the biological characteristics of each of the two materials the position fixation members according to present invention, are preferably of such dimension that, in undeformed condition thereof, the seating portion of the lower position fixation member is spaced further from the optical axis of the lens body than the seating portion of the upper position fixation member.

The position fixation member are preferably integrally joined to the lens body by any one of several known methods. The lens body and the integrally joined position fixation members are inserted in the eye through a corneo-scleral incision for example, and the polypropelene member is seated in the circumferential cul-de-sac portion of the eye between the anterior and posterior capsule walls whereas the other position fixation member i.e. the polymethylmethacrylate position fixation member is seated in the ciliary sulcus of the eye. The resilient spring-like characteristic of the polypropylene position fixation member enables the intraocular lens to be maintained in position without suturing.

More specifically the current invention relates to an intraocular lens suitable for use as an artificial lens implant, preferably one which is intended to seat adjacent to the pupil in the posterior chamber of the eye, and which comprises a medial, light-focusing, lens body and at least a pair of position fixation members connected with the lens body. One of the position fixation members extends generally laterally outwardly from a first region of the periphery of the lens body and is intended to extend to and seat adjacent to the periphery of the iris in the vascular tissue of the ciliary sulcus. The other position fixation member extends generally laterally outwardly from a second region of the periphery of the lens body and is intended to extend to and seat in the non-vascular tissue of the cul-de-sac formed between the anterior and posterior capsules. The one position fixation member comprises a first material preferably polymethylmethacrylate, which is substantially biologically inert to the environment within the eye and exhibits a given springiness, and the other position fixation member comprises a second material, polypropylene, which I believe to be substantially less biologically inert to the environment within the eye than said first material and exhibits a substantially greater springiness than said first material.

According to this invention the position fixation member are not only a different materials having the characteristics described above, but further, are of different length, as measured between the optic axis of the lens body and the seating portion of the respective position fixation member in undeformed condition thereof. Thus, preferably said other position fixation member is about 1 mm longer than said one position fixation member, i.e., said second seating portion is located on the opposite side of and about 1 mm further from the optical axis of the lens than said first seating portion when both position fixation members are in undeformed condition thereof. In all other respects the pair of position fixation members are preferably dimensionally substantially equivalent.

Preferably said one position fixation element has a first seating portion and said other position fixation element has a second seating portion and said first and second materials are such that said second seating portion moves about 2 mm to a position approximately 1 mm closer to the optical center of the lens body than said first seating portion when normal pressure used to seat the lens is applied to each said seating portion.

In its preferred form, the current invention is specific to the use of polypropylene for the lower position fixation member which seats in the capsule, and polymethylmethacrylate for the upper position fixation member which seats in the ciliary sulcus.

The invention accordingly comprises the constructions hereinafter described, the scope of the invention being indicated in the following claims.

Figure 2:
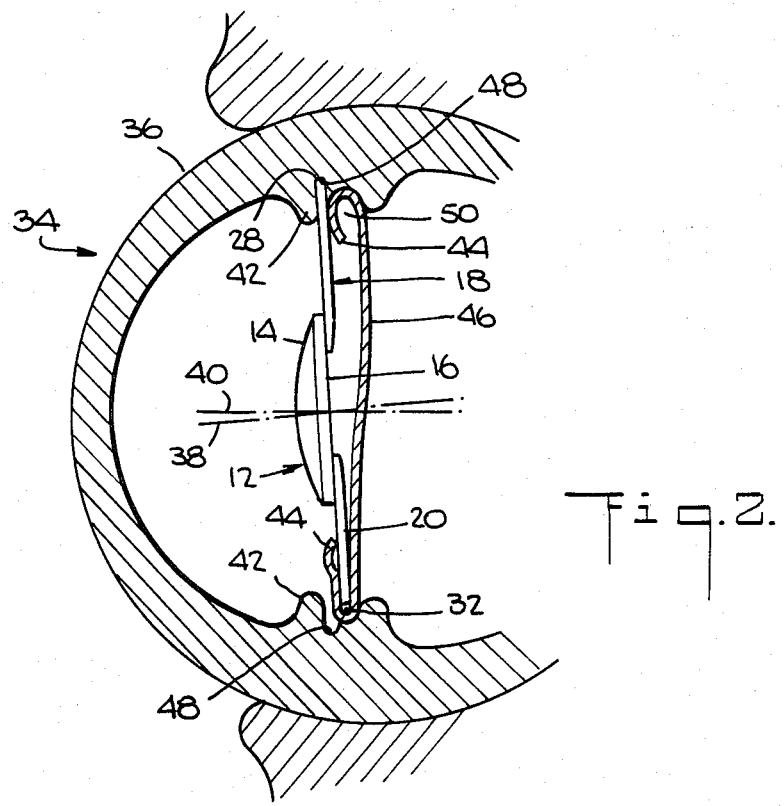

In the accompanying drawing in which the preferred embodiment of the invention is illustrated, FIG. 1 is a simplified plan view of an intraocular lens according to the preferred embodiment of the present invention; and FIG. 2 is a simplified schematic sectional view of an eyeball with the intraocular lens seated therein.

Referring now to the drawing, an intraocular lens according to the preferred embodiment of the invention is generally indicated by reference numeral 10 in FIG. 1.

The intraocular lens includes a medial light-focusing lens body 12 having a convex or flat anterior surface 14 and a generally flat or convex posterior surface 16. A pair of position fixation members 18 and 20 are integrally joined to opposite peripheral sections 22 and 24 of the lens body 12.

The position fixation members 18 and 20 are preferably of J-shaped configuration. The position fixation member 18 has a leg portion 26 extending from the peripheral section 22 and terminates in a curved seating portion 28. The position fixation member 20 has a leg portion 30 extending from the peripheral section 24 and terminates in a curved seating portion 32.

The lens body 12 is formed by any suitable material which is compatible with the environment at the interior of the eyeball, such as a non-toxic plastic, for example, polymethylmethacrylate. In the preferred form of the invention, position fixation member 18 is also formed of polymethylmethacrylate while position fixation member 20 is formed of polypropylene as will be described in more detail below.

Referring to FIG. 2, the intraocular lens 10 is inserted in an eyeball 34 using suitable known medical procedures, which include, for example, a corneo-scleral incision 36.

The lens body 12 has an optical axis 38, which for the sake of simplicity is presumed to be the geometric center of the lens body. It will also be presumed that the eye has an optical axis 40 passing through the center of the pupil formed by the iris 42. The eyeball 34 includes an anterior capsule wall 44 that has been partially removed with the cataract as shown in FIG. 2, and a posterior capsule wall 46. It should be noted that after a cataract removal the upper, i.e. superior, portion of the eye usually has a substantially lesser amount of anterior capsule wall 44 remaining than does the lower, i.e. inferior, portion.

A ciliary sulcus portion 48 of the eye is defined between the iris 42 and the anterior capsule wall 44. The ciliary sulcus 48 extends circumferentially at upper and lower portions of the eye when viewed in cross-section.

A circumferential cul-de-sac portion 50 of the eye is defined between the anterior capsule wall 40 and the posterior capsule wall 46, at upper and lower portions of the eye when viewed in cross-section as shown in FIG. 2. The ciliary sulcus 48 and the circumferential cul-de-sac portion 50 are thus interior peripheral surfaces of the eye 34. The interior surface of the ciliary sulcus 48 is normally spaced approximately 1 to 2 millimeters further from the optical axis 40 of the eye than the interior peripheral surface of the circumferential cul-de-sac portion 50.

In the preferred embodiment of the intraocular lens shown in undeformed condition in FIG. 1, the sealing portion 32 of the position fixation member 20 is located a distance $D_2$ from the optical axis 38 of the lens body 12 and the seating portion 28 of the position fixation member 18 is located a distance $D_1$ from the optical axis 38. In the preferred embodiment of the lens the distance $D_2$ is approximately 1 mm greater than the distance $D_1$. Furthermore, the radial distance $D_1$, $D_2$ of each of the seating portions 28 and 32 from the optical axis of the lens body 12 is preferably greater than the distance between the optical axis of the eye and the interior peripheral surface of the ciliary sulcus 48 of the eye into which the lens is intended to be inserted. However, the stiffness of the position fixation member 20 is less than that of the position fixation member 18 by a predetermined amount so as to enable the seating portion 32 to deflect about 2 millimeters while the seating portion 28 preferably does not deflect at all, or only a relatively negligible amount, when the same predetermined force is applied to both.

When the intraocular insert 10 is implanted in the eye, the seating portions 28 and 32 are deflected toward the optical axis of the eye and resiliently bear against the ciliary sulcus 48 and the circumferential cul-de-sac 50 respectively. The predetermined force previously referred to is thus the force imposed by the ciliary sulcus 48 and the circumferential cul-de-sac 50 on the respective seating portions 28 and 32. Since the seating portion 32 deflects about 2 millimeters more than the seating portion 28 when the same force is applied to both, the seating portion 32 can be disposed in the circumferential cul-de-sac 50 whereas the seating portion 28 can be disposed in the ciliary sulcus 48 without detrimentally affecting the alignment between the optical axis of the eye and the optical axis of the lens body. As the seating portions 28 and 32 are generally coplanar, in a plane which is parallel to the posterior surface 16 of the lens body 12, the lens body 12 is inclined approximately 5°-10° with respect to the vertical, which is within acceptable visual-optical limits.

This invention contemplates the use of different materials for the position fixation members, wherein one material is less stiff than the other, the respective stiffnesses being predetermined to ensure that the seating portion 32 deflects about 2 millimeters more toward the optical axis of the eye than the seating portion 28 under force conditions such as are present in the eye when the intraocular insert 10 is positioned as shown in FIG. 2. Particularly, the invention contemplates the use of polymethylmethacrylate for one of the position fixation members and polypropylene for the other of the position fixation members. In accordance with the invention these materials are used in such a manner that the characteristics exhibited by each are used to full advantage as will now be described in more detail.

The polypropylene material of position fixation member 20 has the following characteristics as compared with the polymethylmethacrylate material of the position fixation member 18:

(i) Polypropylene is, I believe, not nearly as inert as polymethylmethacrylate, which latter is substantially inert, i.e., causes practically no inflammatory reaction in adjacent living tissue and has substantially less tendency than Polypropylene to adhere to living tissue. For example, many thousands of anterior chamber lenses made entirely of Polymethylmethacrylate, with which there has been long term experience, exhibited little or no tendency to adhere to tissue. Polypropylene, sometimes referred to as Prolene, on the other hand, is attacked by the fluid in the eye and undergoes at least some changes in response thereto and to exposure to light, as a result of which Polypropylene was found to develop tiny pits in which white blood cells can accumulate. The pitted Polypropylene thus appears to form a matrix which facilitates rather than retards adhesion of adjacent tissue.

(ii) Neither Polymethylmethacrylate, sometimes referred to as PMMA, nor Prolene, will return to its original undeformed condition after being kept in deformed condition for even a relatively short time, e.g., ten hours. Thus, if maintained in a deformed condition for as little as ten hours, neither will return to its original undeformed condition, even after the external force has been removed.

(iii) PMMA is much more rigid than Prolene, i.e., it is substantially less flexible than Prolene. For example, a force of about 140–150 mg is required to deflect seating portion 28 of member 18 a distance of 1 mm toward the optic axis while a force of only about 18 mg is required to deflect seating portion 32 of member 20 a distance of about 1 mm toward the optic axis. After the lens has been in such deformed condition for about 10 hours, the Prolene and the PMMA materials lose a substantial part of their "memory" and it thereafter requires only about 5–7 mg of force to deflect the PMMA position fixation member and about 0.8 to 1.0 mg to deflect the Prolene position fixation member by a distance of 1 mm. Stated in a different way, the Prolene position-fixation member deflects in excess of 5 times the amount deflected by the PMMA position-fixation member in response to a force of approximately 1 mg magnitude applied to each.

According to the present invention, the Prolene member is seated inferiorly, in the capsule, and the PMMA member is seated superiorly, in the ciliary sulcus. In seating the lens, the fexible position fixation elements, which in undeformed condition are preferably at least as long as the spacing between the upper and the lower grooves of the ciliary body and at least slightly longer than the spacing between the grooves of the eye in which the lens is to be seated, i.e., between the upper ciliary groove and the lower capsule groove, must be deformed inwardly for proper seating. This also results in some pressure being exerted outwardly for maintaining the lens in proper position when the lower position fixation member is properly seated in the capsule. Since the Prolene member is much more flexible than the PMMA member, the Prolene member will deform first and to a substantially greater amount than the PMMA member.

Also, because the aforesaid "pitting" begins to take place, the Prolene position fixation member begins to adhere to the capsule in which it is seated shortly after implantation, so as to secure the lens in position.

In the initial undeformed condition of the preferred lens, the seating portion of the Prolene member is located approximately 1 mm further from the optical center of the lens body than the seating portion of the PMMA member. Upon seating, the Prolene member in the capsule deforms approximately 2 mm more than the PMMA member, which latter hardly deforms at all. This compensates for the difference in radial distance from the optical axis of the eye to the ciliary sulcus on the one hand and to the capsular seating region on the other hand, and allows the lens body to be situated such that its optical axis is substantially in line with the optical axis of the eye.

While the capsular tissue is not living tissue, since it is not vascular tissue, the tissue in the ciliary sulcus, on the other hand, is living tissue. Even though the PMMA member seated therein does not, due to the inert nature of the polymethylethacrylate, adhere to the vascular tissue such as, I believe, it would, if that member were formed of Prolene, as with prior lenses, nevertheless, if the pressure were sufficiently high, the PMMA member would continue to press its way into the soft tissue of the ciliary sulcus and eventually that tissue would "grow around" that member. This would create substantial problems, particularly if, at a later date, it were decided to remove the lens from the patient's eye. However, in accordance with the present invention, since the Prolene position fixation member is substantially softer than would be a second PMMA member, i.e., exerts substantially less spring pressure, the risk of tissue growing around the PMMA member is much less than if spring pressure were continued to be applied by, e.g., two PMMA members. This facilitates removal of the lens at a later date, should such become necessary, particularly since the inferior member, being seated in the capsule, can easily be surgically excised. The novel lens according to the present invention thus used to optimum advantage the various physical characteristics exhibited by the materials Prolene and PMMA.

In the preferred embodiment in which the radial extent $D_2$ of the lower position fixation member 20 is greater than the redial extent $D_1$ of the upper position fixation member 18, it is often possible for the surgeon to seat such lower position fixation member in the capsule prior to inserting the entire lens body through the incision in the cornea. Thus, it is possible to accomplish from outside the eye the maneuvering necessary for seating the lower leg in the capsule. This reduces even further the normal risks attendant to manipulating surgical instruments within the eye. The lens according to the present invention has the added advantage, that the lower position fixation member 20, due to its longer radial length $D_2$, its greater flexibility and its having to accommodate itself to the shorter radius of the capsule, will contact the capsule along a longer circumference than the contact between the upper position fixation member 18 and the ciliary sulcus. Consequently a firmer anchoring of member 20 in the capsule becomes possible.

Except for the difference in the radial extent of the pair of position fixation members 18 and 20, the dimensions of the various components of the intraocular lens 10 are substantially similar to those of the model PC-10, posterior chamber, two loop intraocular lens made by Heyer-Schulte. Preferably, the cross sectional diameter of the members 18, 20 is about 0.15 mm.

It will be apparent from the foregoing that it is the specific nature and characteristics of the specific materials according to the present invention used in the particular way described above which results in the stated advantages.

In view of the above, it will be seen that the several objects of the invention are achieved and other advantageous results attained.

As various changes can be made in the above construction without departing from the scope of the invention, it is intended that all matter contained in the above description or shown in the accompanying drawing should be interpreted as illustrative and not in a limiting sense.

What is claimed is:

1. An intraocular lens suitable for use as an artificial lens implant, the lens comprising:
    a medial, light-focusing, lens body intended to be positioned adjacent to the pupil in the posterior chamber of the eye, and a pair of position fixation members connected with said lens body;
    one of said position fixation members extending generally laterally outwardly from a first region of the periphery of said lens body and intended to extend to and seat adjacent to the periphery of the iris in the vascular tissue of the ciliary sulcus;
    the other of said position fixation members extending generally laterally outwardly from a second region of the periphery of said lens body and intended to extend to and resiliently seat in the non-vascular tissue of the cul-de-sac formed between the anterior and posterior capsules of the eye;
    said one position fixation member comprising a first material which is substantially biologically inert to the environment within the eye and exhibits a given springiness and said other position fixation member comprising a second material which is substantially less biologically inert to the environment within the eye than said first material and exhibits a substantially greater springiness than said first material;
    whereby, when the lens is seated in the eye, the vascular tissue of the ciliary sulcus will be in contact only with said substantially biologically inert material and said substantially less biologically inert material will be in contact only with the non-vascular tissue of the posterior capsule of the eye.

2. The intraocular lens as claimed in claim 1, wherein said first material is polymethylmethacrylate and said second material is polypropylene.

3. The intraocular lens as claimed in claim 1 wherein said other position fixation element is longer, in radial direction, than said one position fixation element.

4. The intraocular lens as claimed in claim 3 wherein said other position fixation member is about 1–2 mm longer in radial direction than said one position fixation member.

5. The intraocular lens as claimed in claim 1, wherein said lens has an optical axis, said one and said other position fixation members are otherwise substantially dimensionally identical, and said first material and said second material have flexibility characteristics such that when a force is applied therebetween, said other position fixation member deflects a substantial distance toward the optical axis of the lens prior to said one position fixation member deflecting more than a negligible toward said optical axis.

6. The intraocular lens as claimed in claim 1 wherein said one position fixation member has a first seating portion and said other position fixation member has a second seating portion and said first and second materials have flexibility characteristics such that said second seating portion moves to a position approximately 1–2 mm closer to the lens body than said first seating portion when normal pressure used to seat the lens is applied to each said seating portion.

7. The intraocular lens as claimed in claim 1 wherein said other position fixation member deflects in excess of five times the amount deflected by said one position fixation member in response to a force of equal magnitude applied to each.

8. The intraocular lens as claimed in claim 1 wherein said first and second materials each have a memory which allows said one and said other position fixation members to return to substantially its initial undeformed condition after remaining deformed for less than approximately 10 hours and said second material has a memory which does not suffice to allow said other position fixation member to return to substantially its initial undeformed condition after remaining substantially deformed for in excess of approximately 10 hours.

9. The intraocular lens as claimed in claim 8 wherein each said material achieves a substantially permanent set after approximately 10 hours.

10. The intraocular lens as claimed in claim 9 wherein said position fixation members are each generally J-shaped filaments of approximately 0.15 mm diameter in cross-section, said first material being such that in order to deform said one position fixation member a distance of 1 mm toward the optical axis of force of approximately 140–150 mg is needed prior to the material acquiring a set and a force of approximately 5–7 mg is needed after the material acquires a set, and in order to deform said other position fixation member a distance of 1 mm toward the optical axis a force of approximately 15–20 mg is needed prior to the material acquiring a set and a force of approximately 0.8–1.0 mg is needed after the material acquires a set.

* * * * *